(12) United States Patent
Colin

(10) Patent No.: US 7,626,050 B2
(45) Date of Patent: *Dec. 1, 2009

(54) DIRECT METHOD FOR SYNTHESISING ALKYLHALOGENOSILANES

(75) Inventor: Pascale Colin, Chassieu (FR)

(73) Assignee: Bluestar Silicones France SAS, Lyons (FR)

( * ) Notice: Subject to any disclaimer, the term of this patent is extended or adjusted under 35 U.S.C. 154(b) by 83 days.

This patent is subject to a terminal disclaimer.

(21) Appl. No.: 10/578,439

(22) PCT Filed: Oct. 27, 2004

(86) PCT No.: PCT/FR2004/002759

§ 371 (c)(1),
(2), (4) Date: Feb. 20, 2007

(87) PCT Pub. No.: WO2005/044827

PCT Pub. Date: May 19, 2005

(65) Prior Publication Data

US 2007/0244337 A1    Oct. 18, 2007

(30) Foreign Application Priority Data

Nov. 5, 2003  (FR) .................................. 03 12969
Jun. 16, 2004 (FR) .................................. 04 06503

(51) Int. Cl.
*C07F 7/00* (2006.01)
(52) U.S. Cl. ....................................... 556/472; 556/473
(58) Field of Classification Search ................ 556/473, 556/472
See application file for complete search history.

(56) References Cited

U.S. PATENT DOCUMENTS

| 4,500,724 A | 2/1985 | Ward, III et al. |
| RE33,452 E | 11/1990 | Ward, III et al. |
| 5,059,343 A * | 10/1991 | Halm et al. ............ 252/182.35 |
| 5,596,119 A | 1/1997 | Halm et al. |
| 5,847,181 A * | 12/1998 | Nakanishi et al. ........... 556/472 |
| 6,005,130 A * | 12/1999 | Lewis et al. ................. 556/422 |
| 6,242,629 B1 * | 6/2001 | Ueno et al. .................. 556/472 |
| 6,258,970 B1 * | 7/2001 | Ward et al. .................. 556/472 |
| 7,202,192 B2 * | 4/2007 | Colin ......................... 502/208 |
| 7,238,638 B2 * | 7/2007 | Colin ......................... 502/208 |

FOREIGN PATENT DOCUMENTS

| DE | 34 25 424 A | 2/1985 |
| EP | 0 778 279 A | 6/1997 |
| EP | 1 156 051 A | 11/2001 |
| EP | 1 173 447 A | 1/2002 |
| FR | 2 848 211 A | 6/2004 |

* cited by examiner

*Primary Examiner*—Shailendra Kumar
(74) *Attorney, Agent, or Firm*—Buchanan, Ingersoll & Rooney P.C.

(57) ABSTRACT

Process for the preparation of alkylhalosilanes by reaction of an alkyl halide, preferably $CH_3Cl$, with a solid body, referred to as contact body, formed of silicon and of a catalytic system comprising ($\alpha$) a copper catalyst and ($\beta$) a group of promoting additives comprising:

an additive $\beta 1$ chosen from metallic zinc, a zinc-based compound and a mixture of these entities, an additive $\beta 2$ chosen from tin, a tin-based compound and a mixture of these entities, optionally an additive $\beta 3$ chosen from cesium, potassium, rubidium, a compound derived from these metals and a mixture of these entities, said direct synthesis process being characterized by the following points, taken in combination:

the copper catalyst ($\alpha$) is in the form of metallic copper, of a copper halide or of a mixture of these entities, the contact body additionally includes a supplementary promoting additive $\beta 4$ chosen from a derivative of an acid of phosphorus and a mixture of these entities.

15 Claims, No Drawings

DIRECT METHOD FOR SYNTHESISING ALKYLHALOGENOSILANES

This application is a 371 of PCT/FR04/02759, filed Oct. 27, 2004.

The present invention relates to improvements relating to the industrial process employed for the direct synthesis of alkylhalosilanes.

The industrial process for the manufacture of alkylhalosilanes and, for example, of dimethyldichlorosilane, subsequently referred to as DMDCS, is a well known process which is disclosed in particular in the United States of America patent U.S. Pat. No. 2,380,995, and in the work by Walter Noll, Chemistry and Technology of Silicones, 1968, published by Academic Press Inc., London, pages 26-41.

According to this "direct synthesis" or "Rochow synthesis" process, the alkylhalosilanes, for example DMDCS, are manufactured directly by reaction of methyl chloride with a solid body, referred to as contact body, formed of silicon and of a catalyst comprising copper, according to the reaction:

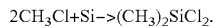

In reality, other coproducts, such as those mentioned below, are formed during the direct synthesis: other alkylhalosilanes, such as methyltrichlorosilane $CH_3SiCl_3$, subsequently referred to as MTCS, and trimethylchlorosilane $(CH_3)_3SiCl$, subsequently referred to as TMCS; halogenated alkylhydrosilanes, such as, for example, methylhydrodichlorosilane $(CH_3)HSiCl_2$, subsequently referred to as MHDCS; and heavy products which are polysilanes and in particular disilanes, such as, for example, trimethyltrichlorodisilane $(CH_3)_3Si_2Cl_3$ and dimethyltetrachlorodisilane $(CH_3)_2Si_2Cl_4$.

With regard to the composition of the contact body, it is known to use copper, taken in the form of metallic copper or in the form of copper-based chemical compounds, as catalyst of the direct synthesis reaction. It is also known, for the purpose of bringing the performance of the direct synthesis to an economically viable level, to add one or more promoting additive(s) to the contact body. These promoting additives can be: zinc or a zinc halide (U.S. Pat. No. 2,464,033); aluminum (U.S. Pat. Nos. 2,403,370 and 2 427 605); tin, manganese, nickel and silver (United Kingdom patent GB-A-1 207 466); cobalt (United Kingdom patent GB-A-907 161); potassium chloride (Soviet patent SU-A-307 650); arsenic or an arsenic compound (U.S. Pat. No. 4,762,940); cesium or a cesium compound (EP-A-1 138 678); an additive chosen from elementary phosphorus, a metal phosphide and a compound capable of providing a metal phosphide in the direct synthesis reaction body (U.S. Pat. No. 4,601,101); specific mixtures of some of the abovementioned entities (FR-A-2 848 124 and FR-A-2 848 211).

It has now been found, and it is this which constitutes the subject matter of the present invention, that:

in the case of the implementation of a direct synthesis where the contact body is formed of silicon and of a catalytic system comprising a copper catalyst and a group of promoting additives based on zinc and on tin, if, on the one hand, the copper catalyst is introduced in the form of metallic copper and/or of a copper halide and, on the other hand, the contact body additionally includes a supplementary promoting additive carefully chosen from the derivatives of the acids of phosphorus, the following are then observed: on the one hand. a substantial improvement in the selectivity for dialkyldihalosilane, and for example for DMDCS, evaluated by the MTCS/DMDCS mean ratio, and, on the other hand, a substantial fall in the content by weight of "heavy" products with respect to the silanes obtained, while maintaining a very satisfactory mean activity of the contact body, said activity being evaluated by weight of the silanes obtained per hour and per kilogram of silicon introduced.

Other advantages related to the implementation of the present invention will become apparent in the continuation of the present account.

The present invention consequently provides a process for the preparation of alkylhalosilanes lanes by reaction of an alkyl halide, preferably $CH_3Cl$, with a solid body, referred to as contact body, formed of silicon and of a catalytic system comprising ($\alpha$) a copper catalyst and ($\beta$) a group of promoting additives comprising:

an additive $\beta 1$ chosen from metallic zinc, a zinc-based compound and a mixture of these entities, an additive $\beta 2$ chosen from tin, a tin-based compound and a mixture of these entities, optionally an additive $\beta 3$ chosen from cesium, potassium, rubidium, a compound derived from these metals and a mixture of these entities, said direct synthesis process being characterized by the following points, taken in combination:

the copper catalyst ($\alpha$) is in the form of metallic copper, of a copper halide or of a mixture of these entities, the contact body additionally includes a supplementary promoting additive $\beta 4$ chosen from a derivative of an acid of phosphorus and a mixture of these entities.

It should be noted that the expression "a derivative of an acid of phosphorus" is intended to denote a phosphorus compound which is entirely different from a metal phosphide (and should not be confused with a metal phosphide), which is known to encompass the combinations and alloys of phosphorus with at least one other metal element, taken in the simple state.

Use may be made, in place of metallic copper, as copper halide, of: a cuprous halide, such as, for example, cuprous chloride; a cupric halide, such as, for example, cupric chloride; and a mixture of these entities. Use is preferably made of metallic copper and/or cuprous chloride.

Use may be made, as supplementary additive $\beta 4$, of: an alkali metal salt, an alkaline earth metal salt or a metal salt of a hypophosphorous acid; an alkali metal salt, an alkaline earth metal salt or a metal salt of a phosphorous acid (ortho, pyro, meta); an alkali metal salt, an alkaline earth metal salt or a metal salt of a hypophosphoric acid; an alkali metal salt, an alkaline earth metal salt or a metal salt of a phosphoric acid (ortho, pyro, meta); an alkali metal salt of a polyphosphoric acid of formula $M_{n+2}(P_nO_{3n+1})$ where M represents an alkali metal and n is a number ranging from 1 to 10; and a mixture of these salts.

Use is preferably made of: an alkali metal salt, an alkaline earth metal salt and/or a copper salt of a hypophosphorous acid, such as, for example, sodium hypophosphite $NaH_2PO_2$ potassium hypophosphite $KH_2PO_2$, calcium hypophosphite $Ca(H_2PO_2)_2$, magnesium hypophosphite $Mg(H_2PO_2)_2$, aluminum hypophosphite $Al(H_2PO_2)_3$ and/or copper(II) hypophosphite $Cu(H_2PO_2)_2$; an alkali metal salt, an alkaline earth metal salt and/or a copper salt of a phosphoric acid (ortho, pyro, meta), such as, for example, trisodium phosphate $Na_3PO_4$, tripotassium phosphate $K_3PO_4$, monocalcium phosphate $Ca(H_2PO_4)_2$, dicalcium phosphate $CaHPO_4$, tricalcium phosphate $Ca_3(PO_4)_2$, basic calcium orthophosphate $Ca_5(PO_4)_3OH$ and/or copper(II) phosphate $Cu(H_2PO_4)_2$; an alkali metal salt of a polyphosphoric acid having the abovementioned formula where n=3, such as, for example, sodium polyphosphate $Na_5P_3O_{10}$.

The amount of additive β4 (calculated as weight of elemental phosphorus with respect to the weight of silicon introduced) lies within the range extending from 50 to 3000 ppm and preferably extending from 80 to 1500 ppm and better still extending from 90 to 1200 ppm; below 50 ppm, the action of the phosphorus cannot really be detected and, above 3000 ppm, the phosphorus has a poison effect which lowers the productive output.

According to a first alternative embodiment of the invention, the supplementary promoting additive β4 is added to the contact body (beside the silicon, copper catalyst and promoting additives β1, β2 and optionally β3) in the state in which it naturally occurs. In the case of this first embodiment, use is more preferably made of sodium hypophosphite $NaH_2PO_2$, potassium hypophosphite $KH_2PO_2$, calcium hypophosphite $Ca(H_2PO_2)_2$, magnesium hypophosphite $Mg(H_2PO_2)_2$, aluminum hypophosphite $Al(H_2PO_2)_3$ and/or copper(II) hypophosphite $Cu(H_2PO_2)_2$. Calcium hypophosphite $Ca(H_2PO_2)_2$ is very specially well suited.

In the case of the first embodiment, the use of 80 to 1500 ppm of said calcium hypophosphite $Ca(H_2PO_2)_2$ is very well suited.

According to a second alternative embodiment of the invention, the supplementary promoting additive β4 is added to the contact body (beside the silicon and promoting additives β1. β2 and optionally β3) in the form of an adduct comprising the copper halide constituting the catalyst (α) and at least one derivative of an acid of phosphorus.

The adduct used in the process in accordance with the invention is a material in the particulate form which is generally employed in the preformed state. For the preparation (carried out beforehand) of the adduct, recourse may be had to any convenient process for mechanically mixing the copper halide with the additive based on at least one derivative of an acid of phosphorus and subsequently rendering homogeneous the mixture thus obtained. It is possible, for example, to mill the copper halide and the additive, both in the form of particles, such as, for example, a powder, the operation being carried out in any mixing device designed for this purpose.

In this second embodiment, use is more preferably made of trisodium phosphate $Na_3PO_4$, tripotassium phosphate $K_3PO_4$, monocalcium phosphate $Ca(H_2PO_4)_2$, dicalcium phosphate $CaHPO_4$. tricalcium phosphate $Ca_3(PO_4)_2$, basic calcium orthophosphate $Ca_5(PO_4)_3$ OH, copper(II) phosphate $Cu(H_2PO_4)_2$ and/or sodium polyphosphate $Na_5P_3O_{10}$. Tricalcium phosphate $Ca_3(PO_4)_2$ and/or basic calcium orthophosphate $Ca_5(PO_4)_3OH$ are very specially well suited.

It has also been found that the fact of using the copper catalyst in this adduct form has the consequence of providing said catalyst with a flowability (which, of course, facilitates the processing thereof) which may be improved with respect to those possessed by the copper halide used alone (that is to say, not in the adduct form).

The amount of additive β4 in the adduct is not of major importance and it can vary within wide limits. According to the invention, it is preferable to use an adduct in the particulate form in which occurs from 0.5 to 10% and better still from 1 to 5% of its weight of additive consisting of at least one derivative of an acid of phosphorus.

In the context of the second embodiment. the use of an adduct in the particulate form in which the copper halide is cuprous chloride and where there is from 1 to 5% of its weight of tricalcium phosphate $Ca_3(PO_4)_2$ and/or of basic calcium orthophosphate $Ca_5(PO_4)_3OH$ is very specially well suited.

The catalyst (α) is generally used, in the case of the first alternative embodiment as in that of the second, at a content by weight ranging from 1 to 20%, preferably ranging from 2 to 12%, with respect to the weight of silicon introduced. In the case of the second alternative embodiment, the amount of catalyst (α) is chosen, within the abovementioned general and preferred regions of variation and according to the composition of the adduct, so as to introduce, into the contact body. a content of derivative(s) of an acid of phosphorus (calculated as ppm of elemental phosphorus with respect to the weight of silicon introduced) which lies within the range extending from 50 to 3000 ppm and preferably extending from 80 to 1500 ppm and better still extending from 90 to 1200 ppm.

In the context of this second alternative embodiment, the use of an amount of adduct based on cuprous chloride and on 1 to 5% of its weight of tricalcium phosphate $Ca_3(PO_4)_2$ and/or of basic calcium orthophosphate $Ca_5(PO_4)_3OH$ which introduces 80 to 1500 ppm of elemental phosphorus is therefore very specially well suited.

According to the embodiment defined above, the catalytic system additionally comprises a promoting additive β1 based on metallic zinc and/or on a zinc compound; use is preferably made of metallic zinc and/or zinc chloride.

The promoting additive β1 is present at a content by weight lying within the range extending from 0.01 to 2%, preferably extending from 0.02 to 0.5% (calculated as zinc metal with respect to the weight of silicon introduced). Up to 90% by weight of the zinc, preferably up to 50% by weight of the zinc, can be replaced by another metal which catalyzes the chlorination of the copper and/or which forms a eutectic or a phase with a low melting point with the copper salts and/or the alkali metal salts. Mention may be made, as metals which may be suitable, of cadmium, aluminum, manganese and silver.

The content by weight of tin and/or of tin compound (promoting additive β2, the content of which is calculated as weight of tin metal) lies within the range extending from 10 to 500 ppm and preferably extending from 30 to 300 ppm, with respect to the weight of silicon introduced.

It is necessary to have at least 10 ppm of tin metal. In addition, a content by weight of greater than 500 ppm would have a harmful effect on the reaction and in particular on the selectivity. Use is made, as tin-based compound, for example. of tin chloride. The promoting additive β2 which is preferably used is tin metal; advantageously, this metallic tin can be added in the form of bronze.

With respect to the optional promoting additive β3, in the case where one of them is used, the following points will be specified:

the content by weight of promoting additive β3 of metal type (calculated as weight of alkali metal with respect to the weight of silicon introduced) lies within the range extending from 0.01 to 2% by weight and preferably extending from 0.05 to 1.0% by weight; below 0.01% by weight, the action of the alkali metal cannot really be detected and, above 2% by weight, the alkali metal does not have the expected effect on the selectivity;

use may be made, as compound of alkali metal chosen from Cs, K and Rb, of: halides and for example the chloride; carboxylates and for example the formate or the acetate; cesium chloride, potassium chloride, rubidium chloride and/or a mixture of these compounds are the promoting additives β3 of metal type which are preferably used.

As for the rest, it is desirable for the particle size of the silicon to be such that the mean diameter of at least 50% by weight of the particles is between 10 and 500 μm and preferably between 60 and 200 μm. Likewise, the catalyst (α) and the group of promoters (β) also occur in the form of particles, the mean diameter of at least 50% by weight of the particles advantageously being between 1 and 100 μm.

The direct synthesis process according to the invention can be carried out generally in one of the three following types of equipment: a reactor of the stirred bed type, such as that disclosed in the United States of America patent U.S. Pat. No. 2,449,821, a reactor of the fluidized bed type, such as that disclosed in the U.S. Pat. No. 2,389,931, or a rotary kiln.

The direct synthesis reaction takes place at a temperature lying within the range extending from 260 to 400° C. and preferably extending from 280 to 380° C. It can be carried out, all or in part, under an absolute alkyl halide pressure equal to atmospheric pressure (1 bar) or greater than atmospheric pressure; when the latter case prevails, the reaction is generally carried out under an absolute pressure extending from 1.1 to 8 bar and preferably extending from 1.5 to 5 bar.

In order to carry out the direct synthesis reaction, an initial stage of activation of the contact body (formed by the combination based on silicon+catalyst+promoters) is advantageously carried out beforehand, as is well known; one of the activation means which is highly suitable can consist in bringing said contact body to a certain temperature which can be less or greater, by a few degrees to a few tens of degrees, than the temperature chosen for the direct synthesis reaction and lie within the general or preferred range mentioned above.

By using the catalytic system ($\alpha$)+($\beta$) according to the invention, it is possible to obtain, when the reaction is carried out, in a stirred bed as in a fluidized bed, at a temperature extending from 260° C. to 400° C. and preferably extending from 280 to 380° C., a high selectivity for dialkyldihalosilane and a low content by weight of heavy byproducts while having a very satisfactory mean activity.

As regards the selectivity, evaluated, for example, by the mean MTCS/DMDCS ratio by weight, the value obtained is of the order of or less than 0.10, being able to reach a value as low as 0.050.

As regards percentage of heavy products formed with respect to the silanes obtained, it is generally less than 3% by weight and it can be as low as 2% by weight.

As regards the mean activity of the catalytic system, it is, for example, of the order of or greater than 120 g of silanes/h/kg Si, being able to reach 200 g of silanes/h/kg Si and even more.

Other advantages and characteristics of the present invention will become apparent on reading the following examples, which are given by way of illustration but without implied limitation.

In the following examples. unless otherwise mentioned, use is made of a cylindrical pilot-scale reactor with an internal diameter of 60 mm and a height of 250 mm equipped at its base with a sintered glass gas distributor. The silicon and the catalytic system are charged in the form of a powder, the mean size of at least 50% by weight of the particles of which is between 60 and 200 μm.

The reaction is carried out in a stirred bed and the reactor is equipped with an external heating element.

COMPARATIVE TEST A:

Catalytic System: $CuCl/ZnCl_2/Sn$

A powder composed of 210 g of silicon, 11.5 g of CuCl, 1.44 g of $ZnCl_2$ and 0.38 g of bronze comprising 10% by weight of tin is charged to a vertical cylindrical glass reactor equipped with a metal stirrer and with a sintered glass gas distributor.

The reactor is gradually heated to 200° C. under a stream of nitrogen. Then, while continuing to raise the temperature of the reactor, the nitrogen valve is closed and the introduction is begun of methyl chloride with a flow rate, measured at 20°C., of 60 g/h.

The temperature of the reactor is adjusted to 315° C. and the methyl chloride flow rate is maintained at 60 g/h for 8 hours. The test takes place at atmospheric pressure.

The mixture produced is analyzed by gas chromatography and it is characterized by:
- an MTCS/DMDCS ratio equal to 0.129 (% by weight/% by weight), and
- a proportion of "heavy products" (polysilanes) amounting to 5.2% by weight.

EXAMPLE 1

Catalytic System: $CuCl/ZnCl_2/Sn/Ca(H_2PO_2)_2$

A powder composed of 210 g of silicon, 11.5 g of CuCl, 1.44 g of $ZnCl_2$, 0.38 g of bronze comprising 10% by weight of tin and 0.576 g of $Ca(H_2PO_2)_2$ (1000 ppm of P with respect to the Si introduced) is charged to a vertical cylindrical glass reactor equipped with a metal stirrer and with a sintered glass gas distributor.

The reactor is gradually heated to 200° C. under a stream of nitrogen. Then, while continuing to raise the temperature of the reactor, the nitrogen valve is closed and the introduction is begun of methyl chloride with a flow rate, measured at 20° C., of 60 g/h.

The temperature of the reactor is adjusted to 315° C. and the methyl chloride flow rate is maintained at 60 g/h for 8 hours. The test takes place at atmospheric pressure.

The mixture produced is analyzed by gas chromatography and it is characterized by:
- an MTCS/DMDCS ratio equal to 0.069 (% by weight/% by weight), and
- a proportion of "heavy products" (polysilanes) amounting to 1.5% by weight.

COMPARATIVE TEST B:

Catalytic System: $CuCl/ZnCl_2/Sn/Cu_3P$

A powder composed of 210 g of silicon, 11.5 g of CuCl, 1.44 g of $ZnCl_1$, 0.38 g of bronze comprising 10% by weight of tin and 2.92 g of copper phosphide $Cu_3P$ comprising 7.2% of phosphorus (1000 ppm of P with respect to the Si introduced) is charged to a vertical cylindrical glass reactor equipped with a metal stirrer and with a sintered glass gas distributor.

The reactor is gradually heated to 200° C. under a stream of nitrogen. Then, while continuing to raise the temperature of the reactor, the nitrogen valve is closed and the introduction is begun of methyl chloride with a flow rate, measured at 20° C., of 60 g/h.

The temperature of the reactor is adjusted to 315° C. and the methyl chloride flow rate is maintained at 60 g/h for 8 hours. The test takes place at atmospheric pressure.

The mixture produced is analyzed by gas chromatography and it is characterized by:
- an MTCS/DMDCS ratio equal to 0.123 (% by weight/% by weight), and a proportion of "heavy products" (polysilanes) amounting to 3.6% by weight.

COMPARATIVE TEST C:

Catalytic System: CuCl/ZnCl$_2$/Sn

A powder composed of 210 g of silicon, 16.4 g of CuCl, 1.64 g of ZnCl$_2$ and 0.38 g of bronze comprising 10% by weight of tin is charged to a vertical cylindrical glass reactor equipped with a metal stirrer and with a sintered glass gas distributor.

The reactor is gradually heated to 200° C. under a stream of nitrogen. Then, while continuing to raise the temperature of the reactor, the nitrogen valve is closed and the introduction is begun of methyl chloride with a flow rate, measured at 20° C., of 60 g/h.

The temperature of the reactor is adjusted to 315° C. and the methyl chloride flow rate is maintained at 60 g/h for 8 hours. The test takes place at atmospheric pressure.

The mixture produced is analyzed by gas chromatography and it is characterized by:
  an MTCS/DMDCS ratio equal to 0.112 (% by weight/% by weight), and
  a proportion of "heavy products" (polysilanes) amounting to 4.0% by weight.

EXAMPLE 2

Catalytic System: CuCl·Ca$_3$(PO$_4$)$_2$/ZnCl$_2$/Sn

A powder composed of 210 g of silicon, 16.4 g of CuCl-Ca$_3$(PO$_4$)$_2$ adduct comprising 2% by weight of Ca$_3$(POA)$_2$, 1.64 g of ZnCl$_2$ and 0.38 g of bronze comprising 10% by weight of tin is charged to a vertical cylindrical glass reactor equipped with a metal stirrer and with a sintered glass gas distributor.

The adduct is prepared by mechanical mixing, the operation being carried out in a Turbula mixer (originating from Prolabo), of CuCl powder (originating from Prolabo) with Ca$_3$(PO$_4$)$_2$ powder (originating from Prolabo).

The reactor is gradually heated to 200° C. under a stream of nitrogen. Then, while continuing to increase the temperature of the reactor, the nitrogen valve is closed and the introduction is begun of the methyl chloride with a flow rate, measured at 20° C., of 60 g/h.

The temperature of the reactor is adjusted to 315° C. and the methyl chloride flow rate is maintained at 60 g/h.

The test takes place at atmospheric pressure. The test is halted by the operator after producing methylchlorosilanes (MCS) for 8 hours.

The mixture produced is analyzed by gas chromatography and it is characterized by:
  an MTCS/DMDCS ratio equal to 0.089 (% by weight/% by weight), and
  a proportion of "heavy products" (polysilanes) amounting to 2.8% by weight.

COMPARATIVE TEST D

Catalytic System: Cu°/ZnCl$_2$/Sn

A powder composed of 210 g of silicon, 21.0 g of metallic copper, 1.64 g of ZnCl$_2$ and 0.38 g of bronze comprising 10% by weight of tin is charged to a vertical cylindrical glass reactor equipped with a metal stirrer and with a sintered glass gas distributor.

The reactor is gradually heated to 200° C. under a stream of nitrogen. Then, while continuing to raise the temperature of the reactor, the nitrogen valve is closed and the introduction is begun of methyl chloride with a flow rate, measured at 20° C, of 60 g/h.

The temperature of the reactor is adjusted to 315° C. and the methyl chloride flow rate is maintained at 60 g/h for 8 hours. The test takes place at atmospheric pressure.

The mixture produced is analyzed by gas chromatography and it is characterized by:
  an MTCS/DMDCS ratio equal to 0.168 (% by weight/% by weight), and
  a proportion of "heavy products" (polysilanes) amounting to 8% by weight.

EXAMPLE 3

Catalytic System: Cu°/ZnCl$_2$/Sn/Ca (H$_2$PO$_2$)$_2$

A powder composed of 210 g of silicon, 21.0 g of metallic copper, 1.64 g of ZnCl$_2$, 0.38 g of bronze comprising 10% by weight of tin and 0.576 g of Ca(H$_2$PO$_2$)$_2$ (1000 ppm of P with respect to the Si introduced) is charged to a vertical cylindrical glass reactor equipped with a metal stirrer and with a sintered glass gas distributor.

The reactor is gradually heated to 200° C. under a stream of nitrogen. Then, while continuing to raise the temperature of the reactor, the nitrogen valve is closed and the introduction is begun of methyl chloride with a flow rate, measured at 20° C., of 60 g/h.

The temperature of the reactor is adjusted to 315° C. and the methyl chloride flow rate is maintained at 60 g/h for 8 hours. The test takes place at atmospheric pressure.

The mixture produced is analyzed by gas chromatography and it is characterized by:
  an MTCS/DMDCS ratio equal to 0.091 (% by weight/% by weight), and
  a proportion of "heavy products" (polysilanes) amounting to 1.7% by weight.

COMPARATIVE TEST E:

Catalytic System: Cu°/ZnCl$_2$/Sn/Cu$_3$P

A powder composed of 210 g of silicon, 21.0 g of metallic copper, 1.64 g of ZnCl$_2$, 0.38 g of bronze comprising 10% by weight of tin and 2.95 g of copper phosphide Cu$_3$P comprising 7.2% of phosphorus (1000 ppm of P with respect to the Si introduced) is charged to a vertical cylindrical glass reactor equipped with a metal stirrer and with a sintered glass gas distributor.

The reactor is gradually heated to 200° C. under a stream of nitrogen. Then, while continuing to raise the temperature of the reactor, the nitrogen valve is closed and the introduction is begun of methyl chloride with a flow rate, measured at 20° C., of 60 g/h.

The temperature of the reactor is adjusted to 315° C. and the methyl chloride flow rate is maintained at 60 g/h for 8 hours. The test takes place at atmospheric pressure.

The mixture produced is analyzed by gas chromatography and it is characterized by:
  an MTCS/DMDCS ratio equal to 0.116 (% by weight/% by weight), and
  a proportion of "heavy products" (polysilanes) amounting to 4.3% by weight.

What is claimed is:

1. A process for the preparation of alkylhalosilanes which comprises reacting an alkyl halide with a solid body formed of silicon in the presence of a catalytic system comprising (α) a copper catalyst and (β) a group of promoting additives, wherein said group comprises:
an additive β1 chosen from metallic zinc, a zinc-based compound or a mixture thereof,
an additive β2 chosen from tin, a tin-based compound or a mixture thereof,
optionally, an additive β3 chosen from cesium, potassium, rubidium, a compound derived from these metals or a mixture thereof, wherein
the copper catalyst (α) is in the form of metallic copper, a copper halide or a mixture thereof, and
the solid body includes a supplementary promoting additive β4 wherein the additive β4 is an alkali metal hypophosphite, an alkaline earth metal hypophosphite, a metal hypophosphite or a mixture thereof.

2. The process as claimed in claim 1, wherein the catalyst (α) is used at a content by weight ranging from 1 to 20%, with respect to the weight of silicon introduced.

3. The process as claimed in claim 1, wherein the content of additive β4 lies within the range extending from 50 to 3,000 ppm.

4. The process as claimed in claim 1, wherein, the additive β4 is added to the solid body in the state in which it naturally occurs.

5. The process as claimed in claim 4, wherein the additive β4 is selected from the group consisting of sodium hypophosphite (NaH2PO2), potassium hypophosphite (KH2PO2), calcium hypophosphite (Ca(H2PO2)2), magnesium hypophosphite (Mg(H2PO2)2), copper(II) hypophosphite (Cu(H2PO2)2), aluminum hypophosphite (Al(H2PO2)3), and mixtures thereof.

6. The process as claimed in claim 4, wherein the additive β4 comprises calcium hypophosphite $Ca(H_2PO_2)_2$.

7. The process as claimed in claim 1, wherein the content of additive β1 lies within the range extending from 0.01 to 2.0%.

8. The process as claimed in claim 1, wherein the additive β31 is metallic zinc or zinc chloride, or mixtures thereof.

9. The process as claimed in claim 1, wherein the content of additive β2 lies within the range extending from 10 to 500 ppm.

10. The process as claimed in claim 1, wherein the additive β2 is tin metal.

11. The process as claimed in claim 10, wherein the metallic tin is introduced in the form of bronze.

12. The process as claimed in claim 1, wherein the content of additive β3, if used, lies within the range extending from 0.01 to 20%.

13. The process as claimed in claim 12, wherein the additive β3 is cesium chloride, potassium chloride, rubidium chloride or a mixture of these compounds.

14. The process as claimed in claim 1, wherein the synthesis reaction is carried out at a temperature lying within the range extending from 260° C. to 400° C., under a pressure equal to or greater than atmospheric pressure.

15. The process as claimed in claim 1, wherein the alkyl halide is $CH_3Cl$.

* * * * *